United States Patent [19]

Bedard

[11] Patent Number: 5,484,586
[45] Date of Patent: Jan. 16, 1996

[54] NAIL POLISH BASE AND METHOD

[76] Inventor: Zetta Bedard, 1033 N. Havenhurst Dr., Los Angeles, Calif. 90046

[21] Appl. No.: 323,516

[22] Filed: Oct. 14, 1994

[51] Int. Cl.$^6$ .................................................. A61K 7/043
[52] U.S. Cl. ............................................. 424/61; 424/401
[58] Field of Search .......................... 424/401, 61, 78.03, 424/682, 665; 514/494

[56] References Cited

U.S. PATENT DOCUMENTS

| | | | |
|---|---|---|---|
| 4,363,796 | 12/1982 | Bouillon et al. | 424/61 |
| 4,547,363 | 10/1985 | Joos | 424/61 |
| 4,708,866 | 11/1987 | Turco et al. | 424/61 |
| 5,093,108 | 3/1992 | Pappas et al. | 424/61 |
| 5,378,798 | 1/1995 | Ehrlich | 528/310 |

Primary Examiner—Thurman K. Page
Assistant Examiner—Sharon Howard
Attorney, Agent, or Firm—Drucker & Sommers

[57] ABSTRACT

A nail polish base coat which promotes the growth of healthy, smooth, thick and strong fingernails and toenails. The nail polish base coat contains calcium, magnesium, zinc, acetylsalicylic acid, Vitamins A, D, and E, ethanol and acetic acid in a water solution. These ingredients are blended with a conventional enamel nail polish base coat to place these ingredients in suspension. By regularly applying the nail polish base coat to the nails, the nails will improve in condition and will be able to be grown out longer.

12 Claims, No Drawings

NAIL POLISH BASE AND METHOD

BACKGROUND OF THE INVENTION

1. Field of the Art

This invention relates to the field of nail polishes and bases, and more particularly to a nail polish base and method which through regular application improves the strength and appearance of a person's fingernails and toenails.

2. Field of the Related Art

Many individuals are greatly concerned with the appearance of their fingernails and toenails. Fingernail bases and polishes have the unfortunate effect of drying, yellowing and making the fingernails brittle, split and crack. The problem of weak fingernails grow worse as one ages and is exacerbated by poor nutrition and illness. In addition, many cancer patients and those suffering from other diseases and conditions experience great difficulty in maintaining healthy and attractive fingernails because their fingernails split, crack, become bumpy and uneven, and fail to grow. Others who have damaged their nails in the past often experience difficulty in growing their fingernails out.

Some prior methods deal with these unattractive and weak fingernails by covering up the problem nails, i.e. by applying acrylic to the nails and then shaping them. However, acrylic nails are relatively costly, use strong smelling chemicals, and must be filled in near the cuticle as the nails grow out. Moreover, acrylic nails may not be appropriate for everyone, i.e. those who are ill.

Other methods attempt to supply essential vitamins, moistening oils, minerals and nutrients to the fingernails in order to improve the condition of the nails by applying nail polishes containing these ingredients. For example, U.S. Pat. No. 4,708,866 to Turco et al. discloses an artificial nail forming composition to shape the fingernails having calcium, vitamins A, B, D and E and other ingredients in a base of mono- and poly- alkyl methacrylate. U.S. Pat. No. 4,363,796 to Bouillon and U.S. Pat. No. 4,919,920 to Devos and U.S. Pat. Nos. 3,887,702 and 3,928,561 to Baldwin disclose fingernail hardening compositions with vitamins and other ingredients. U.S. Pat. No. 5,210,133 to O'Lenick, Jr. refers to vitamins being useful for fingernails. French Patent No. 2568471 disclose nail varnish containing soaps with oxides of magnesium, calcium, zinc and barium added to prevent the nail varnish from sticking to the sides of the walls of the nail varnish bottle. Nothing is said in the French patent about how, if at all, these oxides could or would improve the fingernails.

Notwithstanding these attempts to improve the condition of fingernails, the prior art polishes and nail polish bases failed to adequately improve the condition of the fingernail, and do not promote nail growth.

There accordingly remains a need for a composition and method which can be used to improve the condition of the fingernails by thickening the nails, eliminating ridges and white spots, preventing splitting and brittleness, and aiding the fingernails in growing longer and stronger.

BRIEF DESCRIPTION OF THE INVENTION

The invention provides an improved nail polish base coat which promotes the growth of healthy, smooth, thick, and strong fingernails, comprising:

an enamel base; and calcium, zinc, magnesium, a mild acidic solution, ethanol, an vitamins mixed into suspension with the enamel base.

The invention further provides an improved nail polish base coat which promotes the growth of healthy, smooth, thick and strong fingernails, comprising:

about 1000 mg of calcium, about 400 milligram of magnesium, about 5000 International Units of Vitamin A, about 400 International Units of Vitamin D, about 3200 International units of Vitamin E, about one-quarter teaspoon of powdered zinc gluconate, about one-quarter teaspoon of powdered acetylsalicylic acid, about one and a half tablespoons of an ethanol-water solution, about one and a half tablespoons of a mild acetic acid solution; and enough of an enamel base mixed together with said mixture to make about four fluid ounces of the improved nail polish base coat of the invention.

The invention further provides an improved nail-polish base coat which promotes the growth of healthy, smooth, thick, and strong fingernails, comprising:

an enamel base coat comprising between 80 percent and 95 percent by weight of the improved nail polish base coat; and a blend comprising between about 20 percent and 1 percent by weight of the improved nail polish base coat, said blend comprising by weight about 64 percent vitamin E, about 8 percent zinc, about 8 percent acetylsalicylic acid, about 2.8 percent calcium, about 1.2 percent magnesium, about 8 percent of a mild acetic acid solution, and about 8 percent of neutral grain spirits.

The invention yet further provides a method to promote the growth of healthy, smooth, thick and strong fingernails and toenails, comprising regularly applying a nail polish base coat to the fingernails and toenails, said nail polish base coat comprising:

an enamel base coat into which is mixed calcium, zinc, magnesium, a mild acidic solution, ethanol, Vitamin A, Vitamin D and Vitamin E.

DETAILED DESCRIPTION OF THE INVENTION

The invention provides an improved nail polish base coat having various ingredients which act to improve the health of the nail and nail bed so the fingernail will be smoother with less ridges, have less white spots, will be less brittle and less susceptible to cracking and splitting, and will be able to grow out longer without these conditions occurring. The invention also provides a method to achieve the improved nail appearance by use of the nail polish base.

The nail polish base coat of the invention consists of various additives to a conventional nail enamel polish base formulation. The Applicant has used two different nail polish bases: A conventional acrylic nail polish base and a polyester resin nail polish base. Both function about equally well. The ingredients listing of each type of formulation is set forth below:

Acrylic Nail Polish Base—list of ingredients with largest weight percentage first:

Butyl Acetate

Ethyl Acetate

Nitrocellulose

Toluenesulfonamide Resin

Isopropyl Alcohol

Camphor

Acrylic Resin

D & C #5 yellow

D & C #17 dye

Di-butyl Phthalate

Polyester Nail Polish Base—list of ingredients with largest weight percentage first:

Butyl Acetate

Isopropyl Alcohol

Nitrocellulose

Ethyl Acetate

Acetyl Triethyl Citrate

Polyester Resin

Di-butyl Phthalate

Camphor

Stearalkonium Hectorite

Silica

The polyester nail polish base is formulated by Sher-Mar Cosmetics of Canoga Park, Calif.

To either of the enamel base coats, several additive formulations are mixed in and result in the improved nail polish base coat. The additives are as follows:

100 proof vodka (or neutral grain spirits as an ethanol source)

Distilled white vinegar (as a source of 4% to 6% glacial acetic acid)

Aspirin (as a source of acetylsalicylic acid)

Calcium

Magnesium

Zinc gluconate (as a source of elemental zinc)

Vitamins A, D and E

The ethanol, distilled white vinegar and aspirin optimally stabilize the additives in solution in the nail polish base by providing a slightly acidic solution. In the past, it was difficult to keep the solids suspended in solution without excessive shaking or stirring. The acidified solution largely solves this problem. The zinc gluconate acts to help prevent the formation of white spots on the nails. The calcium supplies essential calcium to the nails. The magnesium is used by the body to help metabolize the calcium. Without the addition of the magnesium, the calcium is not readily available to the fingernails and does little to improve the nail condition. Vitamins A, D, and E supply the nails with vitamins essential for healthy growth. The combination of these ingredients help the nails become thicker, less ridged and brittle, split less, have the ability to be grown out longer.

The inventor finds that the following formulation of the ingredients result in an optimal mixture:

1000 mg of calcium, 400 mg of magnesium, 5000 I.U. of vitamin A, and 400 I.U. of vitamin D, all in powder form ¼ teaspoon of powdered zinc gluconate 2 teaspoons of vitamin E in dry form (3200 I.U.)

¼ teaspoon of powdered aspirin (acetylsalicylic acid)

These dry, powdered ingredients are mixed together along with about 1½ tablespoons of 100 proof vodka (as an ethanol source) and 1½ tablespoons of distilled white vinegar (as a source of 4% to 6% of acetic acid), and stirred into a paste. Thereafter, enough of the enamel base coat is added to the resulting paste to make four fluid ounces of nail polish base coat of the invention. The amounts of zinc and magnesium are not too critical, as trace quantities would appear to function well. The calcium and magnesium is conveniently available as "Dr. Bronner's 'All-One' Calcium-Magnesium Powder."

The nail polish base coat of the invention can be formulated so that the additives comprise between 1 and 20 percent of the total weight of nail polish base. The additive blend comprises, by weight, about 60 to 70 percent vitamin E, about 5 to 10 percent zinc gluconate, about 5 to 10 percent acetylsalicylic acid, about 1 to 4 percent calcium, about 0.5 to 2.0 percent magnesium, about 5 to 10 percent of a mild acetic acid solution of about 3 to 5 percent total acetic acid, and about 3 to 10 percent of neutral grain spirits. The amounts of the various ingredients can be varied from those listed above, and the zinc gluconate can be replaced with elemental zinc.

Applicant is aware that others have attempted to formulate nail polish base coats which utilize various vitamins and calcium in an attempt to help improve the nails' condition. However, these prior art nail polishes do not in fact reduce splitting and aid in growing the nails longer. On the other hand, Applicant's formulation appears to make its active ingredients available to the nail bed, with tremendous improvements. The inventor is not certain the reasons why her formulation is effective, but it is.

The nail polish base coat of the invention will then be applied to the fingernails and/or toenails. The dried nail polish base coat can be overcoated with convention colored nail polish, or left uncoated. Either way, the vitamins and minerals in the nail polish base coat are made readily available to the fingernails and/or toenails and nail bed where they aid the fingernails and toenails in becoming smoother with less ridges, having fewer white spots, becoming thicker with less splits, and becoming stronger so they can be grown out faster and longer.

After just a few weeks of the nails being coated with the nail polish base of the invention, the nails become visibly smoother, stronger, less brittle and can be grown out longer without breaking.

The inventor has tested the nail polish base of the invention on a number of persons. Almost without fail, each person noticed rapid and substantial improvement in their nails and the nails could be grown out longer than before. By continuing the use of the nail polish base of the invention, the quality of the nails remained excellent. Even after discontinuing use of the Applicant's nail polish base, or with occasional use of the nail polish, the fingernails continue to look relatively good and remain longer, stronger, and less brittle than before the application of the nail polish base of the invention.

I claim:

1. An improved nail polish base coat which promotes the growth of healthy, smooth, thick, and strong fingernails, comprising:

an enamel base coat; and calcium, zinc gluconate, magnesium, a mild aqueous acidic solution comprising about four to six percent of acetic acid, ethanol, and vitamins mixed into suspension with the enamel base coat.

2. The improved nail polish base of claim 1, wherein the mild aqueous acidic solution further comprises acetylsalicylic acid.

3. The improved nail polish base of claim 2, wherein the mild acetic acid solution comprises distilled white vinegar.

4. The improved nail polish base of claim 1, wherein the ethanol comprises vodka.

5. The improved nail polish base of claim 1, wherein the vitamins comprise vitamin D, vitamin A and vitamin E.

6. An improved nail polish base coat which promotes the growth of healthy, smooth, thick and strong fingernails, comprising:

about 1000 mg of calcium, about 400 milligram of magnesium, about 5000 International Units of Vitamin A, about 400 International Units of Vitamin D, about 3200 International units of Vitamin E, about grams of powdered zinc gluconate, about 3 grams of powdered acetylsalicylic acid, about one and a half fluid tablespoons of an ethanol-water solution, about one and a half fluid tablespoons of a four to six percent solution of acetic acid; and enough of an enamel base mixed together with said mixture to make about four fluid ounces of the improved nail polish coat of the invention.

7. The improved nail polish base coat of claim 6, wherein the ethanol-water solution consists essentially of 100 proof vodka.

8. An improved nail polish base coat which promotes the growth of health, smooth, thick, and strong fingernails, comprising:

an enamel base coat comprising between 80 percent and 99 percent by weight of the improved nail polish base coat; and a blend of active ingredients comprising between about 20 percent and 1 percent by weight of the improved nail polish base coat, said blend of active ingredients comprising by weight about 64 percent vitamin E, about 8 percent zinc gluconate, about 8 percent acetylsalicylic acid, about 2.8 percent calcium, about 1.2 percent magnesium, about 8 percent of a 4 to 6 percent acetic acid solution, and about 8 percent of neutral grain spirits.

9. A method to promote the growth of healthy, smooth, thick and strong fingernails and toenails, comprising regularly applying a nail polish base coat to the fingernails and toenails, said nail polish base coat comprising:

an enamel base coat; and calcium, zinc gluconate, magnesium, a mildly acidic aqueous solution comprising about four to six percent of acetic acid, ethanol, and vitamins mixed into suspension with the enamel base coat.

10. The method of claim 9, wherein the mildly acidic aqueous solution further comprises acetylsalicylic acid.

11. The method of claim 9, wherein the nail polish base coat comprises about 1000 mg of calcium, about 400 milligram of magnesium, about 5000 International Units of Vitamin A, about 400 International Units of Vitamin D, about 3200 International units of vitamin E, about three grams of powdered zinc gluconate, about three grams of powdered acetylsalicylic acid, about one and a half fluid tablespoons of 100 proof ethanol, about one and a half fluid tablespoons of a four to six percent acetic acid solution; and enough of an enamel base coat mixed together with said mixture to make about four fluid ounces of the improved nail polish base coat of the invention.

12. A method to promote the growth of healthy, smooth, thick and strong fingernails and toenails, comprising regularly applying a nail polish base coat to the fingernails and toenails, said nail polish base coat comprising:

an enamel base coat comprising between 80 percent and 99 percent by weight of the improved nail polish base coat; and a blend of active ingredients comprising between about 20 percent and 1 percent by weight of the improved nail polish base coat, said blend of active ingredients comprising by weight about 64 percent vitamin E, about 8 percent zinc gluconate, about 8 percent acetylsalicylic acid, about 2.8 percent calcium, about 1.2 percent magnesium, about 8 percent of a 4 to 6 percent acetic acid solution, and about 8 percent of neutral grain spirits.

* * * * *